United States Patent
Pulkkinen et al.

(10) Patent No.: US 7,076,291 B2
(45) Date of Patent: Jul. 11, 2006

(54) HEART RATE MONITOR

(75) Inventors: Iiris Pulkkinen, Asema (FI); Eeva Kiuru, Oulu (FI); Tapani Lähdesmäki, Oulu (FI)

(73) Assignee: Polar Electro Oy, Kempele (FI)

( * ) Notice: Subject to any disclaimer, the term of this patent is extended or adjusted under 35 U.S.C. 154(b) by 52 days.

(21) Appl. No.: 10/046,668

(22) Filed: Jan. 14, 2002

(65) Prior Publication Data

US 2002/0107451 A1 Aug. 8, 2002

(30) Foreign Application Priority Data

Jan. 18, 2001 (FI) .................................. 20010113

(51) Int. Cl.
*A61B 5/04* (2006.01)
(52) U.S. Cl. ...................... 600/523; 600/520; 600/522; 482/8
(58) Field of Classification Search ........ 600/519–523, 600/525; 482/8
See application file for complete search history.

(56) References Cited

U.S. PATENT DOCUMENTS

| 5,458,548 A | * | 10/1995 | Crossing et al. ............... 482/6 |
| 5,735,799 A | | 4/1998 | Baba et al. |
| 5,769,755 A | | 6/1998 | Henry et al. |
| 5,876,346 A | | 3/1999 | Corso |
| 6,241,684 B1 | * | 6/2001 | Amano et al. .............. 600/531 |
| 6,345,197 B1 | * | 2/2002 | Fabrizio ..................... 600/519 |

FOREIGN PATENT DOCUMENTS

| EP | 0761163 A2 | 3/1997 |
| EP | 0842635 A1 | 5/1998 |
| JP | 07-213499 | 8/1995 |
| WO | WO 90/00366 | 1/1990 |

OTHER PUBLICATIONS

European Search Report for corresponding Application No. 02100006.2.

* cited by examiner

*Primary Examiner*—Angela D. Sykes
*Assistant Examiner*—Roderick Bradford
(74) *Attorney, Agent, or Firm*—Hoffmann & Baron, LLP

(57) ABSTRACT

The invention relates to a heart rate monitor. The essential point of the invention is that a display element (201) of a display (20) of the heart rate monitor for displaying a settable minimum limit for a heart rate level is located at a first end (211) of a display element unit (210) controlled according to the heart rate level, on the same side of the display as the first end of the display element unit. Similarly, a display element (202) for displaying a settable maximum limit for a heart rate level is located at a second end (220) of the display element unit (210), on the same side of the display as the second end of the display element unit.

24 Claims, 4 Drawing Sheets

HEART RATE MONITOR

BRIEF DESCRIPTION OF THE RELATED ART

The invention relates to heart rate monitors. The invention is applied to a personal non-invasive heart rate monitor. The heart rate monitor equipment may consist e.g. of a conventional two-part device comprising a heart rate transmitter, usually of the transmitter belt type, comprising ECG electrodes, and a wristband receiver unit having a telemetric, inductive or optical connection to the heart rate transmitter and comprising e.g. a microprocessor, display and a user interface. Alternatively, the equipment can be a heart rate measurement apparatus which constitutes one integrated whole, particularly a single wristband, in which case the wristband also comprises a sensor, such as ECG electrodes or a pressure sensor, in addition to the other parts. The sensor may even be an optical heart rate measurement sensor.

Heart rate monitors employ a heart rate limit alarm to direct a user's workout such that the exerciser is given an alarm if the exercise heart rate is at or drops below a minimum limit or the heart rate is at or exceeds a maximum limit. In order for the exercise to be efficient enough but still safe, the heart rate should fall within a certain range.

A heart rate monitor naturally comprises a display comprising the actual display element enabling a measured heart rate level to be shown. This can be implemented using either numerical values per minute, i.e. beats per minute (bpm), or percentages of the maximum heart rate. In addition, heart rate monitors equipped with heart rate limit alarms are known wherein the display comprises display elements for set minimum and maximum heart rate limits.

Furthermore, a heart rate monitor is known whose display, in addition to the actual heart rate level display element and the display elements for the minimum and the maximum heart rate limits, is provided with a display element unit comprising a few dozens of display element segments, three adjacent segments of these display element segments being used at a time as an indicator which changes its place on the basis of the measured heart rate information in order to illustrate the height of a measured heart rate level with respect to the minimum and the maximum limit. In this implementation, however, the element for displaying the minimum heart rate limit and the element for displaying the maximum heart rate limit are located at a great distance from the extreme ends of the indicator's range of movement, i.e. far from the extreme ends of the display element unit. Both extreme ends of the movement range are provided with borderlines generated by additional display segments producing a crosswise line, so the user has to interpret the location of a moving indicator with respect to the borderlines, thus being unable to properly interpret the location of the moving indicator with respect to the display elements indicating the minimum and the maximum limit of a desired heart rate level. The above-described known solution causes serious problems to the readability of the display, particularly when the user glances quickly at the display or when there is some kind of movement between a viewer's eye and the heart rate monitor, which is usually the case while walking or running or the like, when the heart rate monitor is kept in the user's moving hand or e.g. attached to the hand-bar e.g. during a cycling exercise.

SUMMARY OF THE INVENTION

An object of the invention is thus to provide a new heart rate monitor, which avoids problems and disadvantages associated with the known solutions.

In order to achieve the above-mentioned object, the heart rate monitor of the invention is characterized by what is disclosed in the independent claim. Preferred embodiments of the invention are disclosed in the dependent claims.

The invention is based on a new manner of placing the display element displaying the desired minimum heart rate limit and the display element displaying the maximum heart rate limit with respect to the display element segment unit controlled by the heart rate level, trying to eliminate problems caused by a moving exerciser and heart rate monitor to the readability of the display.

An advantage of the invention is fast and easy readability enabling the user to observe and thus control his or her workout in a more reliable manner. In addition, exercising becomes safer since the user is provided with an overall picture of the height of his or her current heart rate level with respect to the minimum and the maximum limit of a desired heart rate level.

BRIEF DESCRIPTION OF THE DRAWINGS

The invention is now described in connection with the preferred embodiments and with reference to the accompanying drawings, in which.

DETAILED DESCRIPTION OF THE PREFERRED EMBODIMENTS

The invention thus relates to a carry-on heart rate monitor measuring a person's heart rate non-invasively, i.e. from outside a body, i.e. in practice on the skin of a person.

The general operation and structure of a hear rate monitor will be discussed first.

Figure 1:
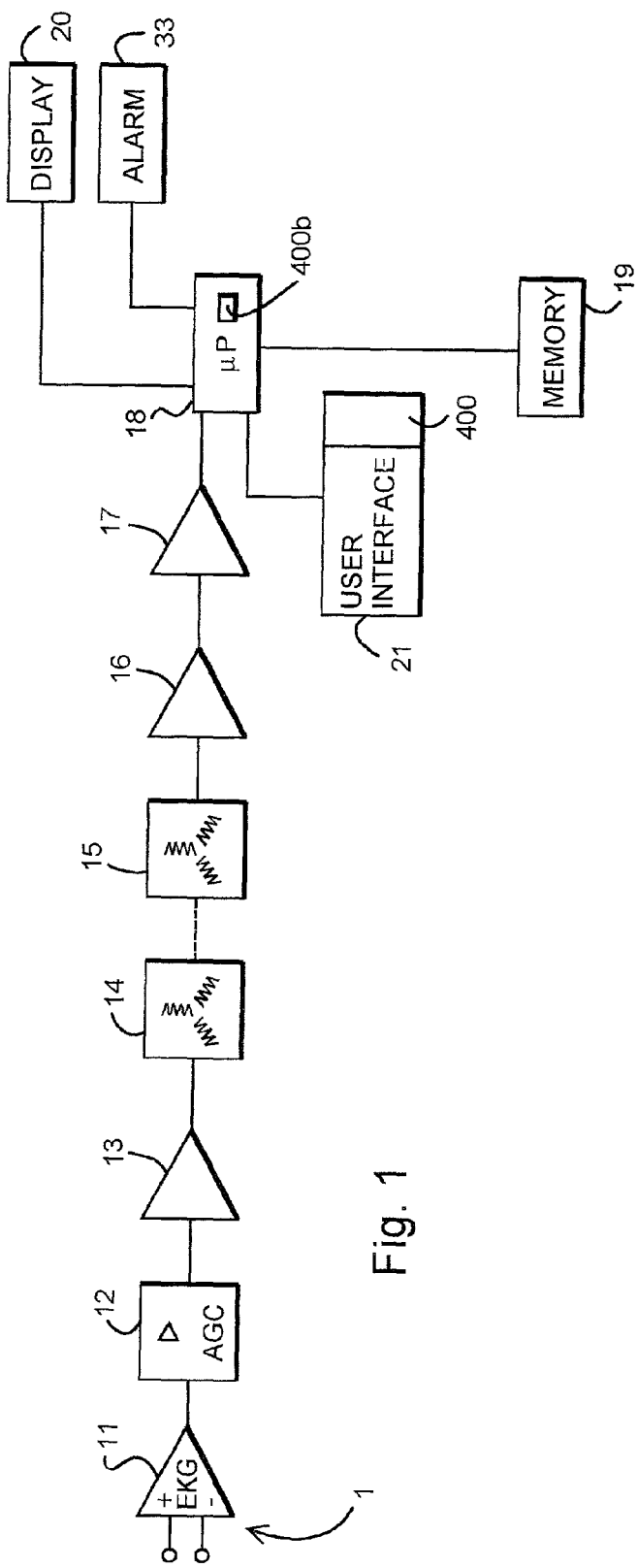
FIG. 1 is a block diagram illustrating a telemetric heart rate measurement arrangement.
Figure 4:
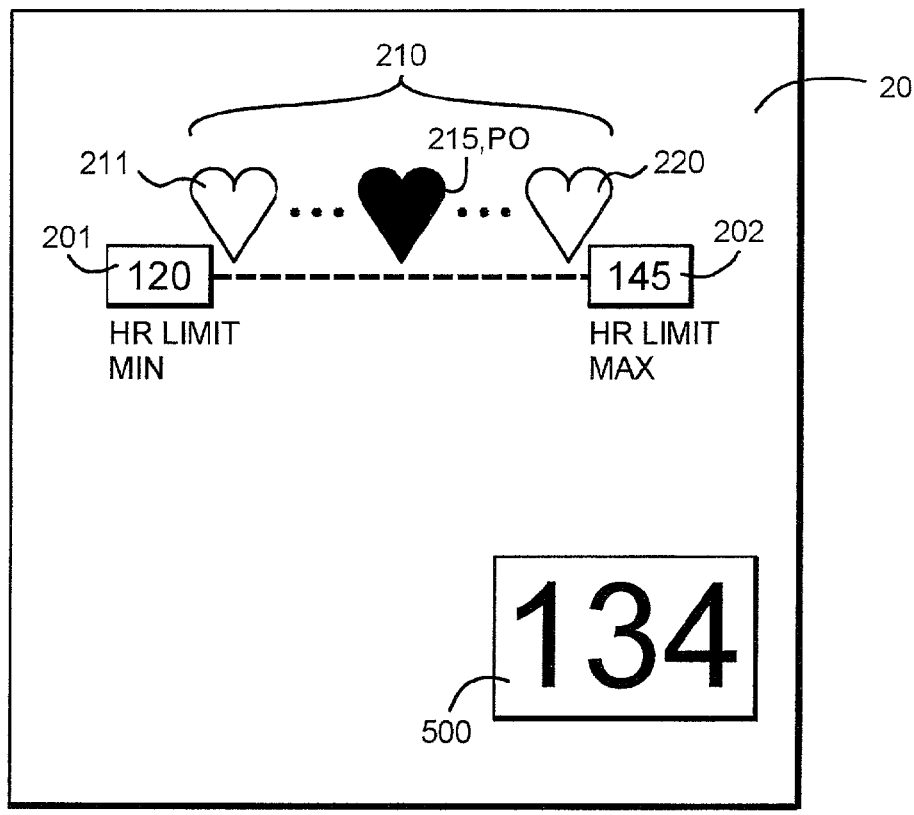
FIG. 4 shows a first embodiment of a display.
Figure 5:
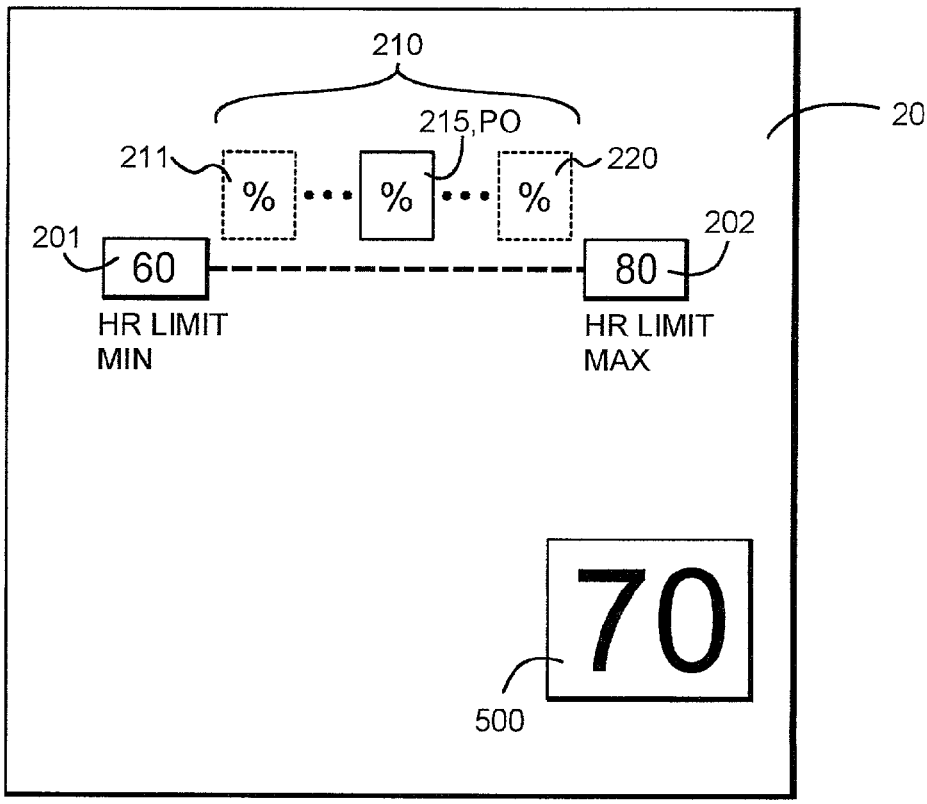
FIG. 5 shows a second embodiment of a display.
Figure 6:
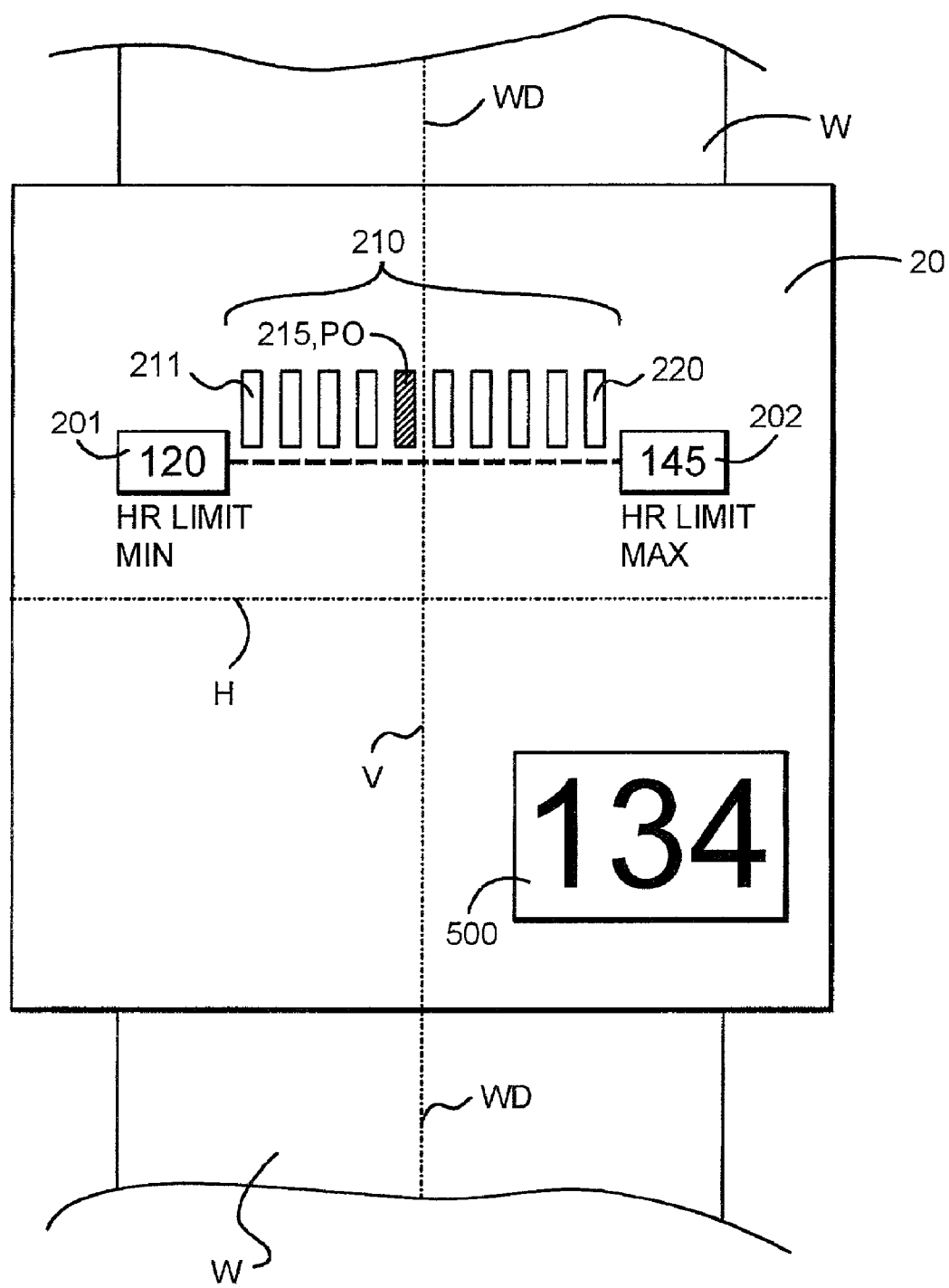
FIG. 6 shows a third embodiment of a display.

FIG. 1 shows a telemetric device for measuring the heart rate, i.e. a heart rate measurement arrangement, which comprises electrodes 1, an ECG preamplifier 11 equipped with differential input poles, an amplifier 12, such as an AGC amplifier, a power amplifier 13, a coil structure 14, 15, a preamplifier 16, a signal amplifier 17, a data-processing unit 18, such as a microcomputer, a memory unit 19 and a display 20, such as a liquid crystal display. In FIG. 1, the electrodes 1 of the telemetric heart rate measurement device are connected to the differential input poles of the ECG preamplifier. A heart rate signal supplied by the preamplifier 11 is amplified in the amplifier 12, e.g. an AGC amplifier, which controls the power amplifier 13 generating an alternating current signal, i.e. a burst signal, according to FIG. 2 to control the coils 14. The magnetic field detected by the receiver coils 15 is amplified in the preamplifier 16, from which the signal is supplied to the signal amplifier 17. An output signal of the signal amplifier 17 is processed in the data-processing unit 18, which stores the heart rate information calculated in the measurement stage in the memory unit 19 and displays the information on the display 20. The implementation of the display 20, which is illustrated in FIGS. 4 to 6, is the most essential part of the invention. In addition, the receiver part may comprise a user interface 21, which may be e.g. a keyboard comprising one or more buttons. The data-processing unit 18 may be e.g. a microprocessor.

The device parts 1 to 14 constitute a measurement and transmitter part A. The device parts 15 to 21 and parts 30 to 33 belong to a receiver part B. Naturally, the transmitter part A and the receiver part B may also comprise other parts than those mentioned above. The measurement and transmitter part A and the receiver part B combine to form a heart rate monitor arrangement.

Figure 2:
FIG. 2 is a schematic view of a burst signal to be fed into magnetic coils of a transmitter unit.

Referring to FIGS. 1 and 2, the transmitters A of the heart rate measurement device typically transmit a burst of about 5 kHz after detecting an ECG signal. A transmitter circuit of the transmitter unit A comprises a resonance circuit, which is activated controlled by a pulse. In addition to a coil 14, the parallel resonance circuit requires a capacitance. The receiver unit B calculates the heartbeat rate, i.e. the heart rate, on the basis of the time difference between successive transmitted signals, i.e. the time difference of bursts, which means that the information to be transmitted, i.e. the heart rate or the heartbeat rate, is included in the transmission, being encoded in the time between burst groups.

Figure 3:
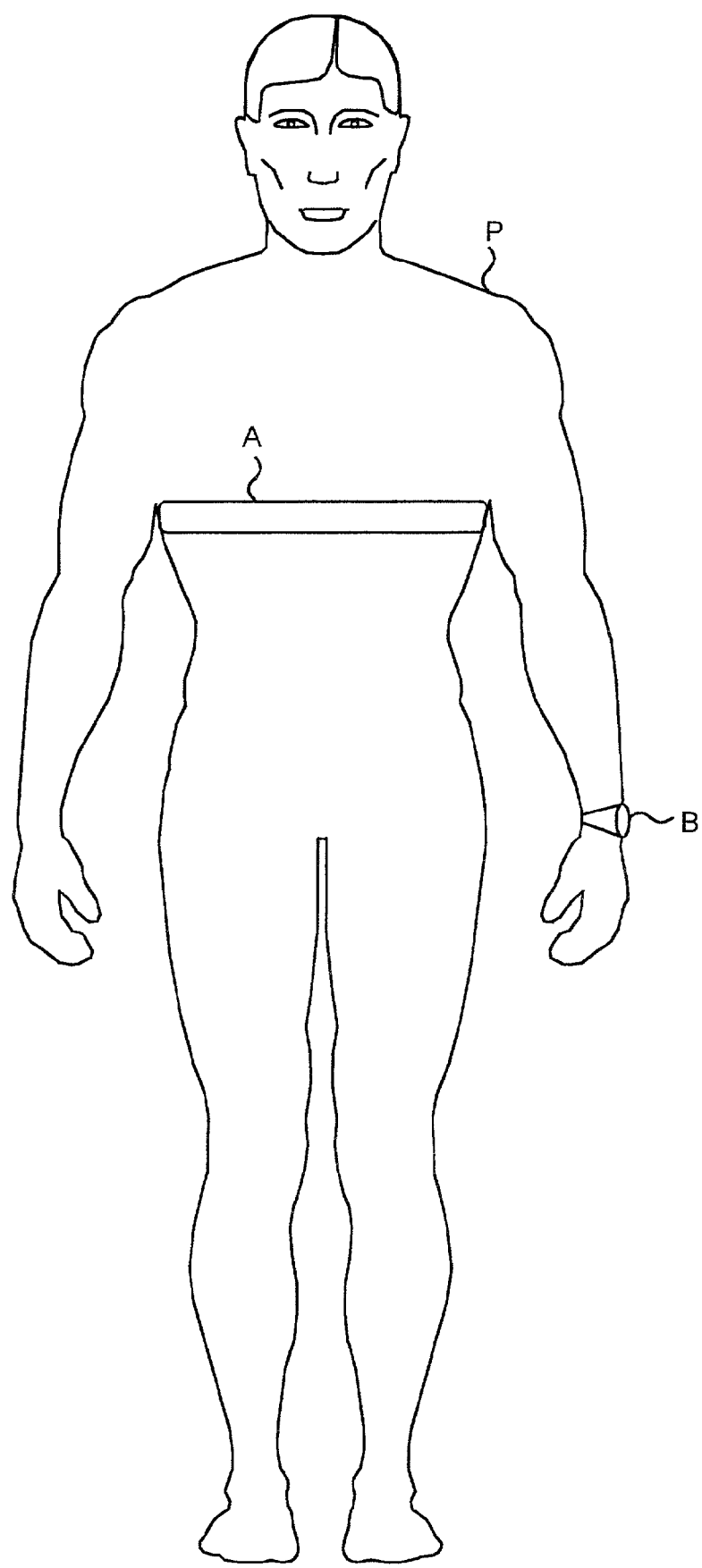
FIG. 3 shows a transmitter unit on a person's chest and a receiver unit on the person's wrist.

Referring to FIGS. 1 and 3, the devices usually comprise the heart rate information measurement and transmitter unit A as a transmitter belt A around the chest of a person P, and by means of the inductive coupling 14, 15 of FIG. 1, measurement information is telemetrically and wirelessly transmitted from the transmitter belt A to the receiver unit B, which is usually implemented as a receiver wristband worn on the wrist of the person P. When applied in connection with a cycling exercise, the receiver unit B may be attached e.g. to the hand-bar of a bicycle. The device is thus a heart rate monitor equipped with a fastening wristband and capable of attachment to a human hand, onto the wrist in particular.

In addition to the two-part version of the device shown in FIGS. 1 and 3, the device may be (not shown) a version wherein the device parts can also be integrated inside a single housing, constituting e.g. a unit with a wristband to be worn for instance exclusively on the wrist or for instance exclusively on the hand-bar of a bicycle. The second version would thus not comprise any separate transmitter unit or receiver unit since the main components would be combined into one integrated whole, i.e. in practice, the electrodes 1 would thus be integrated into the same unit together with the data-processing unit 18 and the display 20. Naturally, the versions would not need all the amplifiers 13, 16, 17 and no coils 14 and 15 according to FIG. 1.

The electrodes 1, ECG amplifier 11, amplifier 12, power amplifier 13 and the coil structure 14, 15 constitute heart rate signal measurement means. The signal measured by the measurement means is modified by heart rate signal modification means comprising a preamplifier 16 and a signal amplifier 17. Only the electrodes 1 can also be considered to constitute the measurement means while the rest of the components, i.e. the ECG preamplifier 11, amplifier 12, power amplifier 13 and the preamplifier 16 following the data transfer and the signal amplifier can be considered to constitute the modification means. On the basis of the received information, the data-processing unit calculates the heart rate and displays related information on the display 20 as a heart rate reading or as a relative proportion of the maximum heart rate.

Referring to FIGS. 4 to 6, the actual contents of the invention, however, relate to the implementation of the display 20.

The display 20 comprises a display element 201 for displaying a settable minimum limit for a desired heart rate level and further, a display element 202 for displaying a settable maximum limit for a desired heart rate level. The display 20 further comprises a display element unit 210 controlled by a measured heart rate level and provided with several display element segments 211 to 220, one or more of the display element segments in the display element unit 210 being used at a time as an indicator PO controlled by the measured heart rate level for illustrating the height of the heart rate level with respect to the minimum limit for the heart rate level and the maximum limit for the heart rate level. The heart rate limits are fed e.g. by means of the user interface 21, i.e. for instance using the keypad 21. The heart rate monitor comprises means 33 for giving an alarm. The means 33 also give an alarm if the heart rate level exceeds the predetermined limits. The data-processing unit 18 can be used for comparing the measured heart rate and the predetermined heart rate limits. The alarm means 33 can be e.g. a piezobuzzer.

The actual invention explicitly relates to the way in which a user is shown the height of the heart rate level with respect to the minimum and the maximum heart rate limit. This is achieved by a new manner of placing the display element 201 displaying a desired minimum limit for the heart rate and the display element 202 displaying a desired maximum limit for the heart rate with respect to the display element segment unit 210, 211 to 220, which illustrates the relative 'position' of the heart rate level and which is controlled by the heart rate level.

An essential point of the invention is that the display element 201 for displaying a settable minimum limit for the heart rate level is located at a first end 211 of the display element unit 210 controlled according to the heart rate level, and that the display element 202 for displaying a settable maximum limit for the heart rate level is located at a second end 220 of the display element unit controlled according to the heart rate level.

As to the terms 'display element unit' 210, 'first end of the display element unit' and 'second end of the display element unit', it is notified that the display element unit illustrates not the heart rate exceeding the limits but explicitly the heart rate within the limits, so the first end of the display element unit refers to the outermost display element segment 211, which is activated when the heart rate is at or exceeds the minimum limit. Similarly, the second end of the display element unit refers to the outermost display element segment, which is activated while the heart rate is still at or below the maximum limit. It is thus stated that in principle there may exist more display element segments beyond the ends of the display element unit but they are activated only if the heart rate exceeds the heart rate limits. The possible 'additional' display element segments activated at heart rates exceeding the heart rate limits are thus not considered to be part of the display element unit 210 since according to the invention, the display element 201 displaying the minimum limit has thus to be located at the first end of the display element unit 201 and the display element unit 202 displaying the maximum limit has to be located explicitly at the second end of the display element unit 210.

In the version shown in FIG. 6, the display element unit 210 controlled according to the heart rate level comprises ten adjacent, narrow and bar-like display element segments 211 to 220. The narrower a single display element segment of the display element unit 210, for instance a segment 215, the more accurate the way in which the indicator PO implemented by one or more display element segments is able to indicate the relative height of the current heart rate. In order to improve the illustrative performance, the display element unit may also comprise a scale 250, in which case the indicator PO points to the scale 250, preferably being located in the immediate vicinity of the scale. In the version according to FIG. 6, the indicator PO can be implemented by one single display element segment. In the version of FIG. 4, the indicator PO is heart-shaped. In a preferred embodiment, the heart-shaped indicator PO, or an indicator having an otherwise curvilinear shape or a shape otherwise different from the narrow, line-like bar, is implemented by a display of the dot matrix type whose dots can be activated separately, i.e. each dot constitutes a separate display element segment of its own. Preferably, the indicator PO thus tapers towards one end, comprising a top 230; this gives the indicator a special pointing effect. In the preferred embodiment, at least a part of the indicator PO extends to the projection area between the display element 201 displaying the minimum limit for the heart rate level and the display element displaying the maximum limit for the heart rate level. This enables the indicator, or at least the top thereof, and the entity comprising the display unit displaying the minimum heart rate limit and the display unit displaying the maximum heart rate limit to be readily integrated into a narrow area that can be read quickly.

Readability is also enhanced e.g. by directing the display element unit 210, 211 to 220 controlled on the basis of the measured heart rate level such that the direction of motion of the indicator controlled on the basis of the measured heart rate level is substantially parallel to the reading direction of the display elements for the minimum and the maximum limit of the heart rate level. In the examples of the figures, the reading direction is the horizontal direction, i.e. the crosswise direction with respect to the direction WD of a wristband W.

In order to enhance the readability, in the preferred embodiment of the heart rate monitor according to the invention, the display element 201 for displaying a settable minimum limit for the heart rate level and the first end 211 of the display element unit controlled according to the heart level are located on the same side of the display with respect to both the center line H of the display parallel to the reading direction of the display and the center line V of the display perpendicular to the reading direction of the display. Similarly, the display element 202 for displaying a settable maximum limit for the heart rate level and the second end 220 of the display element unit controlled according to the heart level are located on the same side of the display with respect to both the center line H of the display parallel to the reading direction of the display and the center line V of the display perpendicular to the reading direction of the display. In the heart rate monitor, the display element 201 for displaying a settable minimum limit for the heart rate level and the first end 211 of the display element unit 210 controlled according to the heart level are thus located on the same side as the display element 202 for displaying a settable maximum limit for the heart rate level and the second end 220 of the display element unit controlled according to the heart level.

Comparing FIGS. 4 and 5, it can be seen that the heart rate monitor comprises at least two display modes. Referring to FIG. 4, it can be seen that in a first display mode, the minimum and the maximum limit for the heart rate level are shown as heart rate readings, i.e. the display element 201 displays the figure 120 as the set minimum heart rate limit while the display element 202 displays the figure 145 as the set maximum heart rate limit. The figures refer to beats per minute (bpm). Referring to FIG. 5, it can be seen that in a second display mode, the minimum and the maximum limit for the heart rate are shown as a proportion of the maximum heart rate, i.e. in practice as a percentage of the maximum heart rate. In the example of FIG. 5, the minimum limit is 60% of the maximum heart rate while the maximum limit is 80% of the maximum heart rate.

The heart rate monitor comprises means 400 for selecting a display mode from a set of at least two display modes, i.e. from a set comprising at least a first and a second display mode. At least to some extent, the means 400 can be considered to be part of the user interface 21. The means 400 can control the data-processing unit 18 that may comprise additional means 400b for changing the display mode. The means 400, 400b enable the mode of the display 20 to be changed as shown in FIGS. 4 and 5.

In the implementation of the operation of the invention, the device blocks used in the invention can be implemented by software, as an ASIC circuit, using separate components or as a desired combination of the above.

Comparing FIGS. 4 and 5, it can be seen that in the heart rate monitor according to the preferred embodiment, the indicator PO controlled on the basis of the measured heart rate level and located in the display element unit is different in the second and the first display mode. In the display mode according to FIG. 4, the indicator is heart-shaped. In the display mode according to FIG. 5, the indicator PO is e.g. a square provided with a percent sign in connection thereof, i.e. inside the square or in the vicinity thereof. In the preferred embodiment, the means 400 for changing the display mode are arranged to change the indicator PO controlled on the basis of the measured heart rate level in accordance with the display mode. The means 400 for changing the display mode are arranged to change the same display mode for the display element 201 for displaying the minimum limit for the heart rate level, the display element 202 for displaying the maximum limit for the heart rate level and for the actual main display element 500 of the heart rate level contained in the heart rate monitor. The display mode of the indicator PO is thus also changed at the same time as the display modes of the rest of the elements 201, 202 and 500 of the display. The above implementations make the heart rate monitor easier to use.

It is obvious to one skilled in the art that as technology advances, the basic idea of the invention can be implemented in many different ways. The invention and its embodiments are thus not restricted to the above examples but may vary within the scope of the claims.

The invention claimed is:

1. A carry-on heart rate monitor measuring a person's heart rate non-invasively, the heart rate monitor comprising a display for displaying heart rate information about a heart rate signal measured on the person, the display comprising a display element for displaying a settable minimum limit for a desired heart rate level, a display element for displaying a settable maximum limit for a desired heart rate level, a display element unit controlled by the measured heart rate level and provided with a plurality of display element segments, at least one of the display element segments being activated in response to the measured heart rate level and graphically representing the measured heart rate level by a position of the at least one activated display element segment relative to the display element for displaying the settable minimum limit for the desired heart rate level and the display element for displaying the settable maximum limit for the desired heart rate level, wherein the display element for displaying a settable minimum limit for the heart rate level is located at a first end of the display element unit controlled according to the heart rate level, on the same side of the display as the first end of the display element unit, and that the display element for displaying a settable maximum limit for the heart rate level is located at a second end of the display element unit controlled according to the heart rate level, on the same side of the display as the second end of the display element unit, the heart rate monitor adapted for being a carry-on heart rate monitor.

2. A heart rate monitor as claimed in claim 1, wherein the display element for displaying a settable minimum limit for the heart rate level and the first end of the display element unit controlled according to the heart rate level are located on the same side of the display with respect to both a center line of the display parallel to the reading direction of the display and a center line of the display perpendicular to the reading direction of the display.

3. A heart rate monitor as claimed in claim 2, wherein the display element for displaying a settable maximum limit for the heart rate level and the second end of the display element unit controlled according to the heart rate level are located on the same side of the display with respect to both a center line of the display parallel to the reading direction of the display and a center line of the display perpendicular to the reading direction of the display.

4. A heart rate monitor as claimed in claim 1, wherein the display element for displaying a settable maximum limit for the heart rate level and the second end of the display element unit controlled according to the heart rate level are located on the same side of the display with respect to both a center line of the display parallel to the reading direction of the display and a center line of the display perpendicular to the reading direction of the display.

5. A heart rate monitor as claimed in claim 1, wherein the display element for displaying a settable minimum limit for the heart rate level and the first end of the display element unit controlled according to the heart rate level are located on the same side of the display as the display element for displaying a settable maximum limit for the heart rate level and the second end of the display element unit controlled according to the heart rate level.

6. A heart rate monitor as claimed in claim 1, wherein the display element unit controlled on the basis of the measured heart rate level is directed such that the direction of motion of the indicator controlled on the basis of the measured heart rate level is substantially parallel to the reading direction of the display elements for the minimum limit and the maximum limit of the heart rate level.

7. A heart rate monitor as claimed in claim 1, wherein the heart rate monitor comprises means for selecting a display mode from a set of at least two display modes, i.e. a set comprising at least a first and a second display mode.

8. A heart rate monitor as claimed in claim 7, wherein in a first display mode, the minimum limit and the maximum limit for the heart rate level are shown as heart rate readings.

9. A heart rate monitor as claimed in claim 8, wherein in a second display mode, the minimum limit and the maximum limit for the heart rate level are shown as a proportion of the maximum heart rate.

10. A heart rate monitor as claimed in claim 8, wherein the means for changing the display mode are arranged to change the same display mode for the display element for displaying the minimum limit for the heart rate level, the display element for displaying the maximum limit for the heart rate level, and for the actual main display element for the heart rate level contained in the heart rate monitor.

11. A heart rate monitor as claimed in claim 7, wherein in a second display mode, the minimum limit and the maximum limit for the heart rate level are shown as a proportion of the maximum heart rate.

12. A heart rate monitor as claimed in claim 11, wherein the means for changing the display mode are arranged to change the same display mode for the display element for displaying the minimum limit for the heart rate level, the display element for displaying the maximum limit for the heart rate level, and for the actual main display element for the heart rate level contained in the heart rate monitor.

13. A heart rate monitor as claimed in claim 7, wherein the means for changing the display mode are arranged to change the same display mode for the display element for displaying the minimum limit for the heart rate level, the display element for displaying the maximum limit for the heart rate level, and for the actual main display element for the heart rate level contained in the heart rate monitor.

14. A heart rate monitor as claimed in claim 1, wherein the indicator controlled on the basis of the measured heart rate level and located in the display element unit is different in the second and the first display mode.

15. A heart rate monitor as claimed in claim 14, wherein the means for changing the display mode are arranged to change the indicator controlled on the basis of the measured heart rate level in accordance with the display mode.

16. A heart rate monitor as claimed in claim 15, wherein the means for changing the display mode are arranged to change the same display mode for the display element for displaying the minimum limit for the heart rate level, the display element for displaying the maximum limit for the heart rate level, and for the actual main display element for the heart rate level contained in the heart rate monitor.

17. A heart rate monitor as claimed in claim 14, wherein the means for changing the display mode are arranged to change the same display mode for the display element for displaying the minimum limit for the heart rate level, the display element for displaying the maximum limit for the heart rate level, and for the actual main display element for the heart rate level contained in the heart rate monitor.

18. A heart rate monitor as claimed in claim 1, wherein the heart rate monitor is a heart rate monitor equipped with a fastening wristband and capable of attachment to a human hand, onto the wrist in particular.

19. A heart rate monitor as claimed in claim 1, wherein the heart rate monitor comprises means for measuring a heart rate signal, means for modifying the signal measured by the measurement means, data-processing means for finding out the heart rate level from the signal modified by the modification means, the data-processing means being connected to the display, and a user interface for controlling the operation of the heart rate monitor.

20. A heart rate monitor as claimed in claim 1, wherein a direction of motion resulting from activation of at least one display element segment is substantially parallel to a reading direction of the display element for displaying the minimum limit of the desired heart rate level and the display element for displaying the maximum limit of the desired heart rate level.

21. A heart rate monitor as claimed in claim 1, wherein the display element segments are spaced apart from each other.

22. A heart rate monitor as claimed in claim 1, wherein the display element for displaying a settable minimum limit comprises a numeric display.

23. A heart rate monitor as claimed in claim 1, wherein the display element for displaying a settable maximum limit comprises a numeric display.

24. A heart rate monitor as claimed in claim 1, wherein a direction of motion resulting from activation of at least one display element segment is substantially parallel to a center line H that is substantially parallel to a reading direction of at least one of the display element for displaying the minimum limit of the desired heart rate level and the display element for displaying the maximum limit of the desired heart rate level.

* * * * *